United States Patent [19]

Theeuwes et al.

[11] 4,088,864
[45] May 9, 1978

[54] PROCESS FOR FORMING OUTLET PASSAGEWAYS IN PILLS USING A LASER

[75] Inventors: Felix Theeuwes, Los Altos; Richard J. Saunders, San Jose; Wayne S. Mefford, Los Altos, all of Calif.

[73] Assignee: Alza Corporation, Palo Alto, Calif.

[21] Appl. No.: 660,219

[22] Filed: Feb. 23, 1976

Related U.S. Application Data

[63] Continuation of Ser. No. 524,585, Nov. 18, 1974, abandoned.

[51] Int. Cl.² ............................................. B23K 27/00
[52] U.S. Cl. ............................ 219/121 LM; 219/384; 128/260; 206/.5; 424/15
[58] Field of Search ........................... 424/15, 14, 19; 128/260; 206/.5; 264/312; 219/121 LM, 121 L, 121 EB, 384; 423/659

[56] References Cited

U.S. PATENT DOCUMENTS

| 216,107 | 6/1879 | Richards ................................ 424/15 |
| 3,404,254 | 10/1968 | Jones ............................. 219/121 EB |
| 3,562,377 | 2/1971 | Zetzsche ............................. 264/312 |
| 3,620,759 | 11/1971 | Maddox .............................. 424/15 X |
| 3,808,394 | 4/1974 | Mominee et al. ................ 219/384 X |
| 3,823,816 | 7/1974 | Controulis et al. ................ 424/15 X |
| 3,965,327 | 6/1976 | Ehlscheid et al. ........... 219/121 LM |

OTHER PUBLICATIONS

Precise Perforations Every Time, Silvus et al. 11-1969, Tool & Manufacturing Engineer.

Primary Examiner—Bruce A. Reynolds
Assistant Examiner—Mark H. Paschall
Attorney, Agent, or Firm—Thomas E. Ciotti; Paul L. Sabatine; Edward L. Mandell

[57] ABSTRACT

A high speed process and apparatus are disclosed for forming outlet passageways of accurate, predetermined size in the walls of pills which dispense their contents by osmotically pumping said contents out said outlet passageways. The pills are moved in succession by an indexer past a passageway forming station where the pills are tracked seriatim at the velocity at which they are moving by an optical tracking system focused on the pill wall and into which a laser beam is directed. During the tracking the laser is fired and the laser beam is transmitted by the optical tracking system onto the wall of the moving pill, the laser power, laser beam dimensions and firing duration being such as to cause the laser beam to heat and pierce the pill wall, thereby forming said outlet passageway.

5 Claims, 10 Drawing Figures

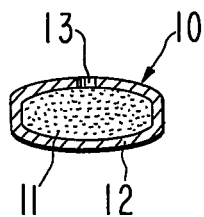
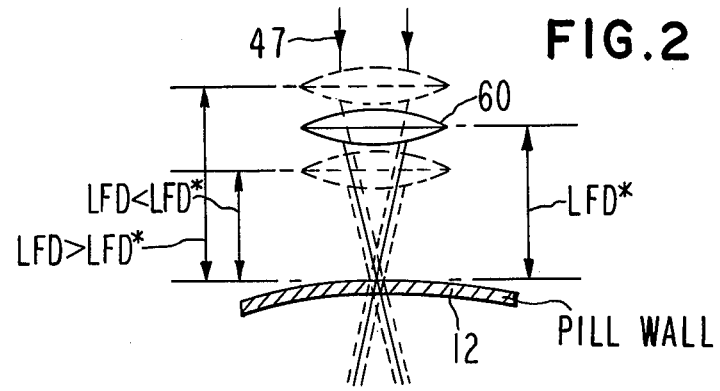
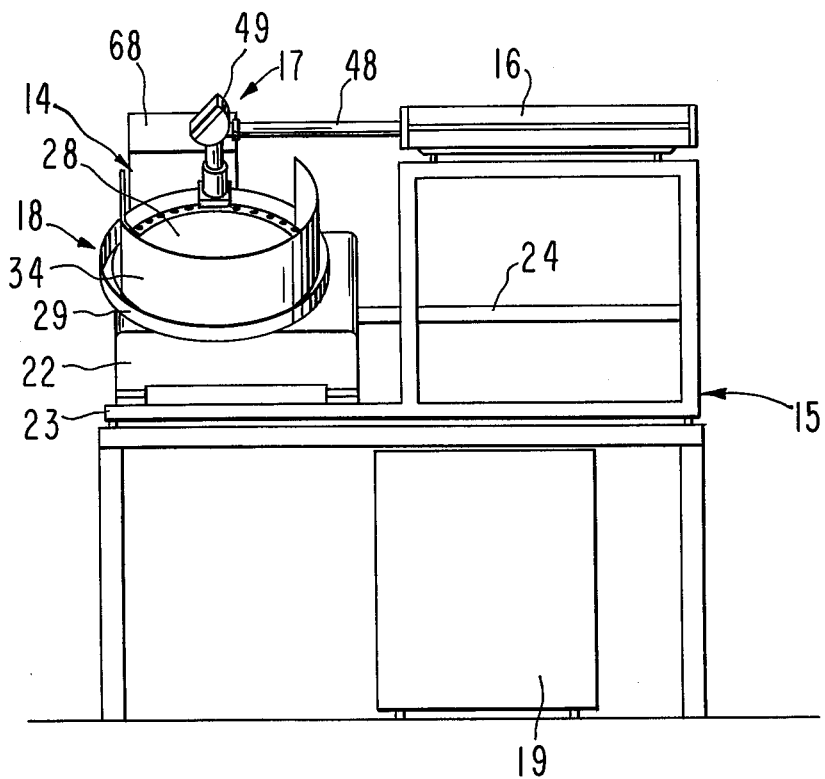
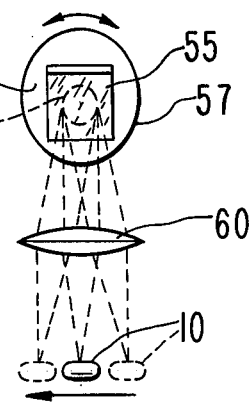

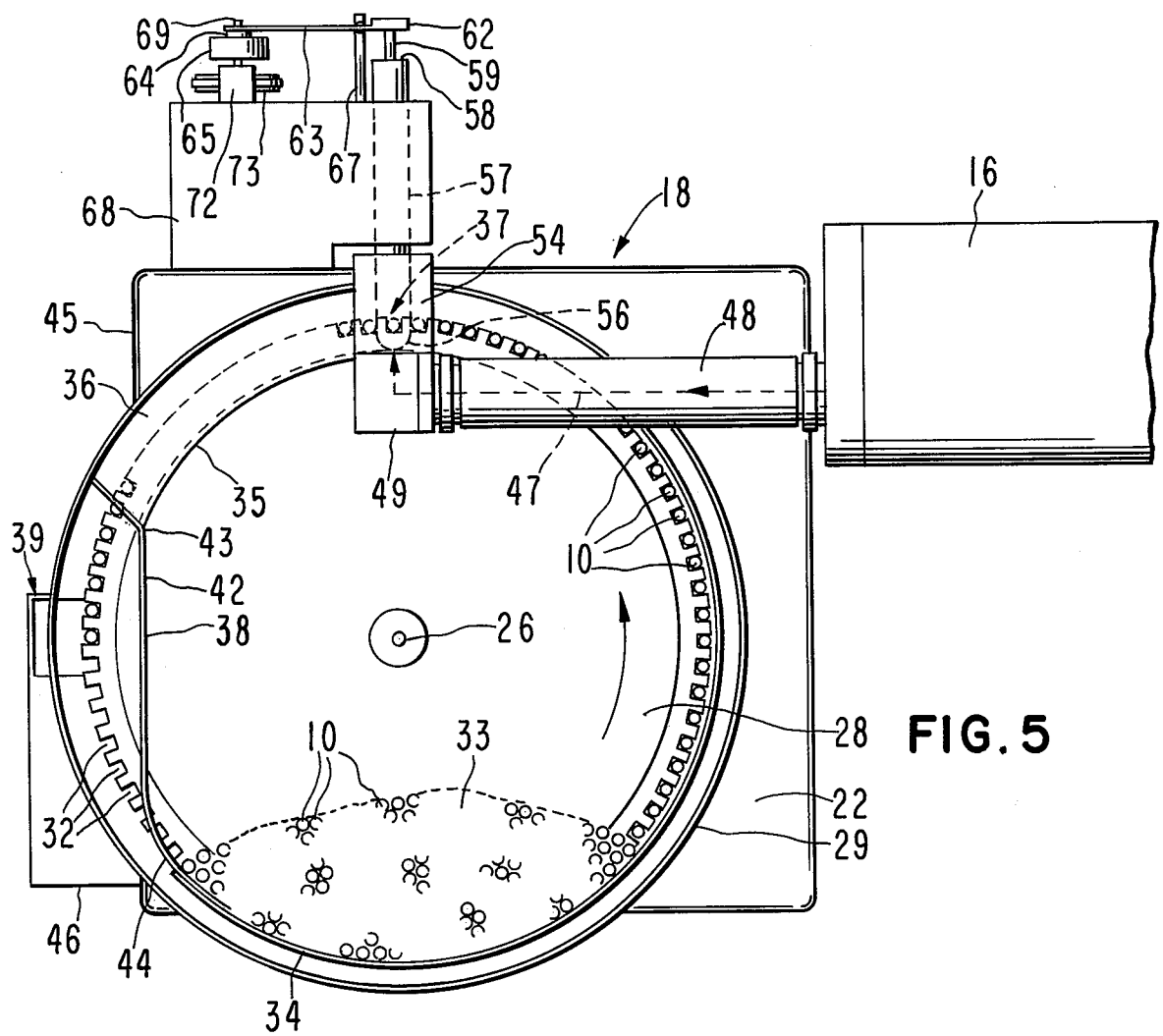
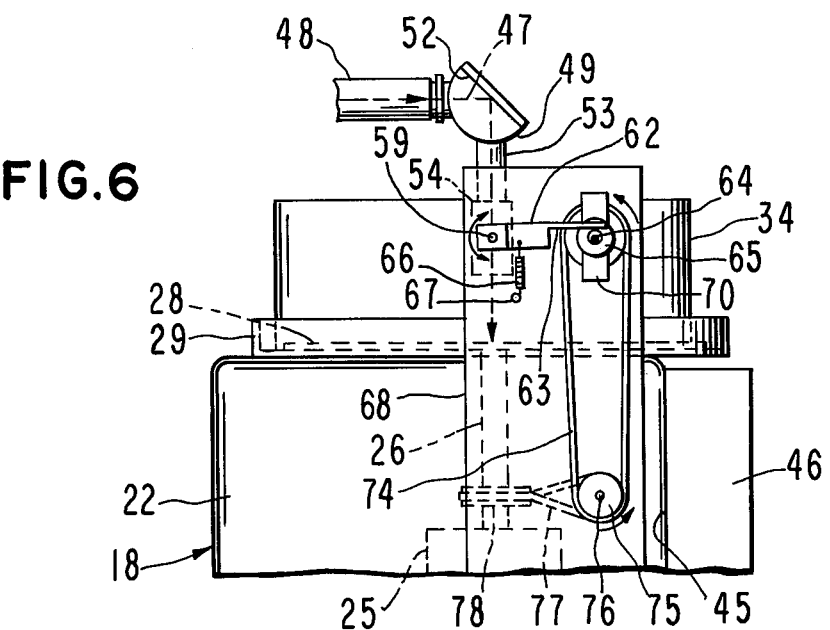

PROCESS FOR FORMING OUTLET PASSAGEWAYS IN PILLS USING A LASER

This is a continuation, of application Ser. No. 524,585, filed Nov. 18, 1974, now abandoned.

BACKGROUND OF THE INVENTION

1. Field of the Invention

This invention relates to a process for forming outlet passageways in the walls of pills which dispense their contents by osmotically pumping the contents out the outlet passageway using a laser. More specifically it relates to a high speed process for forming the outlet passageways in the walls of the pills described in copending applications Ser. Nos. 259,469 and 440,281 filed June 5, 1972 and Feb. 7, 1974, respectively, with a laser.

2. Description of the Prior Art

U.S. Pat. No. 3,146,169 describes pharmaceutical tablets comprising a water soluble drug core partially enclosed by a layer of water insoluble material. These tablets are made by compression coating techniques in which holes are mechanically punched through the water insoluble layer to effect partial enclosure of the core and provide exposure sites thereto by gastrointestinal fluids.

Lasers have been used to bore holes in watch jewels (U.S. Pat. No. 3,601,576), perforate thermoplastic sheets (U.S. Pat. No. 3,617,702), form holes in baby bottle nipples (U.S. Pat. No. 3,524,046) and perforate chemical-containing plastic packets ("Precise Perforations Every Time", Silvus et al, *The Tool and Manufacturing Engineer*, Nov. 1969, pp. 46–49). Defensive publication T903,014 discloses using a laser to print on pharmaceutical tablets.

SUMMARY OF THE INVENTION

The invention is a process for forming outlet passageways of accurate, predetermined size in the walls of pills which dispense their contents by osmotically pumping said contents out said outlet passageway. The pills to which this process applies are described in commonly assigned, copending applications Ser. Nos. 259,469 and 440,281, filed June 5, 1972 and Feb. 7, 1974, respectively, the disclosures of which are herein incorporated by reference.

The size of these outlet passageways is critical since the passageways function as pump exit ports which must not permit a significant amount of the pill's contents to escape by diffusion while allowing the pumping action to occur without excessive pressure build-up inside the pill. The invention process provides a way of forming such passageways accurately, rapidly, reliably and without contaminating the pill's contents.

The invention process comprises: moving the pills in succession along a predetermined path at a predetermined velocity; tracking the moving pills seriatim at said velocity with a laser of a wavelength which is absorbable by the walls; and firing the laser during the tracking, the laser beam dimensions at said wall, the laser power and the firing duration being such as to cause the laser beam to heat and pierce the wall to the extent that an outlet passageway 4 to 2000 microns in diameter is formed in the wall.

In preferred embodiments of the above described process: the path is circular; the tracking is done by reflecting the laser beam from an oscillating mirror such that the beam repeatedly sweeps a predetermined section of the path; the beam passes through a focusing lens, and the wall of the pill during said tracking is positioned at a distance from said lens such that the laser beam is diverging at its point of contact with said wall.

BRIEF DESCRIPTION OF THE DRAWINGS

In the drawings FIG. 1 illustrates the pills to which the invention process applies, FIGS. 3–6 illustrate apparatus for carrying out the invention process and FIGS. 2 and 7–10 illustrate relationships between the passageway size and shape and certain variables in the invention process. Specifically:

FIG. 1 is an enlarged cross section of a pill to which the invention process applies;

FIG. 2 is a schematic view illustrating the effect the position of the laser beam focusing lens to the pill wall has on the size and shape of the outlet passageway;

FIG. 3 is a partly schematic, front elevational view of apparatus for carrying out the invention process;

FIG. 4 is a schematic, diagrammatic view of the pill tracking means of the apparatus of FIG. 3;

FIG. 5 is a top plan view of a portion of the apparatus of FIG. 3;

FIG. 6 is a rear elevational view of a portion of the apparatus of FIG. 3 illustrating the drive mechanism which synchronizes the pill movement with the laser tracking and firing;

FIG. 7 is a graph showing the relationship between the passageway size and the distance of the lens from the pill wall at a fixed wall thickness, laser power and firing duration; and FIGS. 8, 9 and 10 are graphs showing the relationship between passageway size, wall thickness and firing duration at a fixed laser power at three different pill wall-to-lens distances.

DETAILED DESCRIPTION OF THE INVENTION

Figure 7:
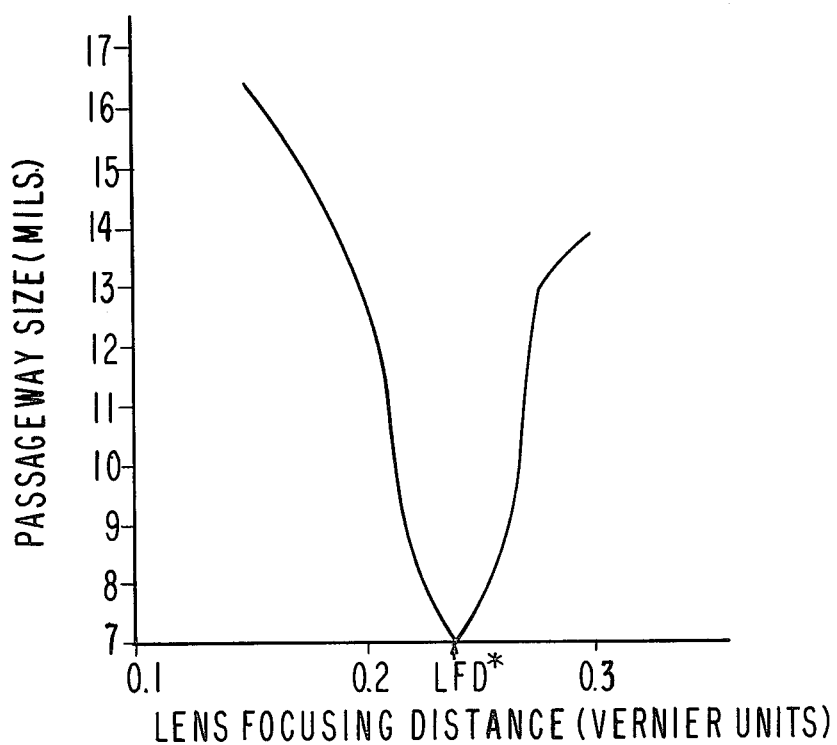

FIG. 1 shows an embodiment, generally designated 10, of the pills to which the invention process applies. Pill 10 comprises an inner core 11 surrounded by a wall 12 having an outlet passageway 13 (as formed per the invention process) in it. Core 11 must comprise a material which is an osmotically effective solute. In this respect it may comprise an active agent, such as a drug, which is itself an osmotic attractant or an active agent which itself is either an osmotically effective solute or not admixed with an inert osmotically effective solute additive such as an organic salt or a sugar. Wall 12 is formed at least in part of a semipermeable material, that is, it is permeable to the inward passage of water from the environment of use, e.g., gastrointestinal fluid, but substantially impermeable to the outward passage of the material(s) comprising core 11. Wall 12 will usually be between about 0.1 to 2000 microns thick. Since wall 12 functions as a pump housing it must maintain its integrity (not distend or disintegrate substantially) over the dispensing lifetime of pill 10. Materials from which osmosis and reverse osmosis membranes are made may be used to make wall 12. Examples of such materials are cellulose acetate, plasticized cellulose triacetate, agar acetate, amylose triacetate, $\beta$-glucan acetate, acetaldehyde dimethyl acetate, cellulose acetate ethyl carbamate, cellulose acetate phthalate, cellulose acetate succinate, cellulose acetate dimethaminoacetate, cellulose acetate ethyl carbonate, cellulose acetate chloroacetate, cellulose acetate ethyl oxalate, cellulose acetate methyl sulfonate, cellulose ethers, poly(vinyl methyl) ether copolymers, cellulose acetate octoate, methyl cellulose, polyurethanes, hydrolyzed polyvinylacetate and hydroxylated ethylenevinylacetate copolymer.

Pill 10 dispenses its contents, i.e., core 11 as follows. Pill 10 is placed in an aqueous environment, such as a body cavity if core 11 contains a pharmaceutical. Core 11, being an osmotic attractant, causes water to permeate from the environment inwardly through wall 12. The water which has permeated through wall 12 dissolves a portion of the osmotically effective solute of core 11, forming a saturated solution. That solution exerts a hydrostatic pressure inside the device thereby dispensing the solution from the pill 10 out passageway 13.

As indicated above passageway 13 is critically sized to permit pill 10 to operate as an osmotic pump. In this regard passageway 13 must not be so large as to permit a significant amount of core 11 to diffuse outwardly through it relative to the amount of core 11 which is osmotically pumped out it (the ratio of amounts should be less than about 0.1:1) and must not be so small as to cause pressure to accumulate within pill 10 in excess of that which would burst wall 12 open. It has been found that passageways in the range of about 4 microns to about 2000 microns in diameter will usually meet the above described functional criteria. Preferably the passageway diameter will be in the range of about 75 microns to about 350 microns.

FIG. 3 depicts apparatus, generally designated 14, for forming passageway 13. Apparatus 14 includes a support frame, generally designated 15, a laser 16, an optical pill tracking mechanism, generally designated 17, a rotary pill indexer, generally designated 18, and an electrical power supply/control 19 which supplies and controls the power for laser 16, tracking mechanism 17 and indexer 18.

Indexer 18 is the portion of apparatus 14 which moves pills 10 in succession along a predetermined path at a predetermined velocity. It is substantially identical in structure and operation to the pill indexer units used in the pharmaceutical industry to print trademarks, designs or other designations on pills. Indexer 18 includes a housing 22 which is bolted to frame members 23, 24 (FIG. 3). Because the vertical position of frame member 23 is lower than the vertical position of frame member 24, indexer 18 is inclined rearwardly. As discussed hereinafter this inclination facilitates charging the pills to indexer 18. An electrical motor 25 (FIG. 6) is contained within housing 22 and is connected (not shown) to power supply 19. Motor 25 has a driving shaft 26 which extends upwardly through an aperture (not shown) in the top 27 of housing 22. An indexing wheel 28 is fixedly mounted on the end of driving shaft 26. Wheel 28 sits freely within a drum 29 attached to top 27 of housing 22 and has a plurality of slots 32 spaced equidistantly around its periphery. Slots 32 are adapted in size and shape to receive pills 10 (FIG. 5). As seen in FIG. 5 a hopper at 33 for pills 10 is defined by the upper surface of wheel 28 and by a fixed arcuate wall 34 which extends upwardly from the bottom of drum 29 and around and closely adjacent to about half the periphery of wheel 28. Pills 10 fall by gravity from the hopper at 33 into slots 32 with their bottoms engaging the surface of the bottom of drum 29. A cover 35 comprising a generally horizontal wall 36 and an integral generally vertical wall (not shown) encloses a section of the edge of wheel 28 immediately downstream from a passageway forming station (indicated generally at 37). Cover 35 prevents pills 10 in which a passageway 13 has been formed from returning to the hopper 33. A generally vertical wall 38 joins cover 35 and wall 34 and prevents pills 10 in hopper 33 from being discharged from indexer 18 at the pill discharge station thereof, indicated at 39. Wall 38 is comprised of a chordal portion 42 having an end 43 joined to cover 35 and an integral arcuate portion 44 which extends into overlapping adjoinment with the inner surface of wall 34. The lower edge of wall 38 is spaced just above the surface of wheel 28.

As seen in FIG. 6 portions of wheel 28 and drum 29 overhang the side 45 of housing 22. Drum 29 has a hole (not shown) in the bottom of its overhanging portion through which pills 10 in which a passageway 13 has been formed may drop. A collecting bin 46 is positioned below that hole to catch the pills 10 dropping therethrough.

Optical tracking mechanism 17 is the portion of apparatus 14 which receives a beam (indicated by a dashed line 47 in FIGS. 2 and 6) from laser 16 and tracks the pills 10 being carried in the slots 32 of wheel 28 seriatim with the beam. Beam 47 is generated within laser 16 which is mounted horizontally on the top of support frame 15. The wavelength of the laser beam should be readily absorbable by the material of wall 12 of pill 10. Most of the wall 12 materials described hereinbefore efficiently absorb energy in the range of 9-12 microns wavelength. Conventional $CO_2$ lasers produce a beam of approximately 10.6 microns wavelength and accordingly may be used with most wall materials. Lasers having higher or lower wavelengths than a $CO_2$ laser may be used, but the absorbtion of their energy output by the pill wall will be less efficient. The use of such lasers will require greater power and/or firing duration to form passageways 13. For use in the invention process laser 16 must be adapted to operate in a pulsed mode, desirably at an average power in the range of 1 to 100 watts and preferably in the range of 15 to 30 watts in the case of a $CO_2$ laser.

Beam 47 exits from laser 16 and travels horizontally through a tubular shield 48, an end of which is coupled to the exit port of laser 16 and the other end of which is coupled to one end of a hollow elbow 49 (FIG. 5). A 45° angle mirror 52 housed within elbow 49 reflects beam 47 90° downwardly (FIG. 6) into tubular member 53 which is coupled to the other end of elbow 49.

The lower end of tube 53 is coupled to a hollow housing 54 (FIG. 6). A second 45° angle mirror (not shown) having a rearward decline is mounted within housing 54 in the path of beam 47. As shown diagrammatically in FIG. 5 beam 47 is reflected by said second 45° angle mirror 90° rearwardly onto a tracking mirror 55 (FIG. 4) affixed to front end 56 of cylindrical tracking mirror mount 57. End 56 is elliptical in shape and declines rearwardly at a 45° angle (i.e. it defines a cylindrical section at 45° to the axis) and thus tracking mirror 55 also declines rearwardly at a 45° angle. Tracking mirror 55 reflects beam 47 90° in a generally downward path in the plane of the major axis of end 56 through a focusing lens 60 (FIG. 4) mounted in housing 54. Mount 57 extends generally horizontally through the rear wall of housing 54 to a position such that tracking mirror 55 is aligned directly above the slotted edge of wheel 28 at tracking station 37. Mount 57 is journalled and received within housing 54 such that it is free to oscillate rotationally (illustrated by solid double arrowheaded lines in FIGS. 4 and 6).

FIGS. 5 and 6 illustrate the mechanism which drives tracking mechanism 17, that is oscillates mount 57, in time with the rotation of wheel 28. Rear end 58 of mount 57 has an axial shaft 59 extending from it. One end of a cam follower 62 is fixedly attached to the end of shaft 59. The other end of follower 62 forms a lever arm 63 which rides on an eccentric pin 64 of a cam wheel 65. The engagement between arm 63 and pin 61 is maintained by a spring 66 attached between follower 62 and a horizontal rod 67 which extends rearwardly from the back of extension 68 of housing 22. Cam wheel 65 is attached to an end of a shaft 69 which is journalled in a C-shaped saddle 72 and within extension 68. Shaft 69 has a driven timing sheave 73 positioned inwardly of cam wheel 65. A timing belt 74 connects sheave 73 with a pulley 75 mounted on a shaft 76 journalled within extension 68. Shaft 76 also carries another pulley (not shown) inwardly of pulley 75 which is connected by a belt 77 to a pulley 78 mounted on shaft 26 of motor 25.

The above described passageway forming apparatus 14 operates as follows. Pills 10 in which passageways 13 are to be formed are charged into hopper 33 and drop by gravity from hopper 33 into slots 32 of rotating feed wheel 28 (FIG. 5). Wheel 28 carries the pills in a circular path at a velocity determined by the speed of motor 25 to passageway forming station 37. At station 37 each pill is tracked by optical tracking mechanism 17 which sweeps repeatedly approximately 1° of the arc of the circular path along which the pill 10 is being carried by wheel 28. As shown in FIG. 4 the tracking is accomplished by the rotational oscillation of mount 57 and tracking mirror 55. The tracking velocity is synchronized with the velocity at which pill 10 is moving because tracking mechanism 17 and wheel 28 are both driven by motor 25. During the tracking laser 16 is fired and emits beam 47. The firing is triggered by a magnetic sensor (not shown) located at a fixed position relative to cam wheel 65 which responds to a magnetic button (not shown) imbedded in the surface of cam wheel 65. As cam wheel 65 rotates, each pass of the magnetic button past the sensor triggers the laser. As mentioned above laser 16 is adapted to pulse mode operation and the duration for which beam 47 is emitted will depend on the pulse setting of laser 16. The duration must, of course, be correlated with the other process variables described herein. Durations in the range of about 0.1 to about 10 milliseconds will usually be employed. Beam 47 is transmitted by optical tracking mechanism 17 onto the surface of the moving pill 10 and moves with the moving pill (FIG. 4) as mirror 55 oscillates clockwise. The energy of beam 47 is absorbed by the material of wall 12 of pill 10, causing the material to heat and ultimately be pierced by the beam, thus forming passageway 13.

At the completion of the tracking mirror 55 oscillates counterclockwise back to its starting position to track the next succeeding pill.

Hole forming station 37 may optionally be equipped with means for maintaining the focusing lens-to-pill wall distance constant despite variations in the overall pill thickness. This means (not shown in the drawings) may comprise a vertically adjustable reference shoe which surrounds but does not interrupt the optical path of the laser beam and is affixed to the lens housing and extends downwardly therefrom such that the distance from the lens to the bottom edge of the shoe is equal to the desired lens to pill wall distance. Combined with the reference shoe is means, such as a spring or air jet, underlying station 37 which engages the pill and urges it upwardly against the bottom edge of the reference shoe while the pill is at station 37.

After a pill 10 clears hole forming station 37 it continues to be carried in a circular path by wheel 28. Cover 35 and wall 38 prevent any pill in which a passageway has been formed and which is prematurely ejected from the slot 32 in which it is riding from returning to hopper 33. When the laser drilled pills 10 reach discharge station 39 they drop through the hole in the bottom of the overhanging portion of drum 29 into bin 46.

Assuming efficient absorbtion of the laser beam 47 by the material of wall 12, the size of passageway 13 will depend upon the laser power, firing duration (pulse time), thickness of wall 12 and the dimensions of beam 47 at the wall 12. As illustrated in FIG. 2 the dimensions of beam 47 at wall 12 also affect the shape of passageway 13 and are a function of the distance between focusing lens 60 and wall 12. In FIG. 2 the distance between the lens and the wall 12 is generally designated LFD (lens focusing distance), with LFD* designating the LFD which is equal to the focal length of the lens. When LFD is less than LFD* wall 12 is struck with a convergent beam causing passageway 13 to be frustoconical in shape rather than cylindrical. When LFD is equal to or greater than LFD* wall 12 is confronted by a divergent beam which, it has been found, forms a generally cylindrical hole. For this reason it is desirable that LFD's equal to or greater than LFD* be employed.

It was also found that when the other aforementioned variables are held constant, that the smallest passageway is formed when LFD = LFD*. This is graphically shown in FIG. 7. The plot of FIG. 7 was developed with a $CO_2$ laser (Coherent Radiation Model 42) set at 50 watts power and 0.6 millisecond firing duration. The wall was 65 microns thick cellulose acetate. Passageways were formed at various LFD's (reported as the vernier reading on the lens vertical adjuster) and measured with an optical comparator. It should be noted that the vernier LFD readings are inversely related to the actual LFD, that is, lesser vernier LFD readings denote greater actual LFD's and vice versa.

Figure 8:
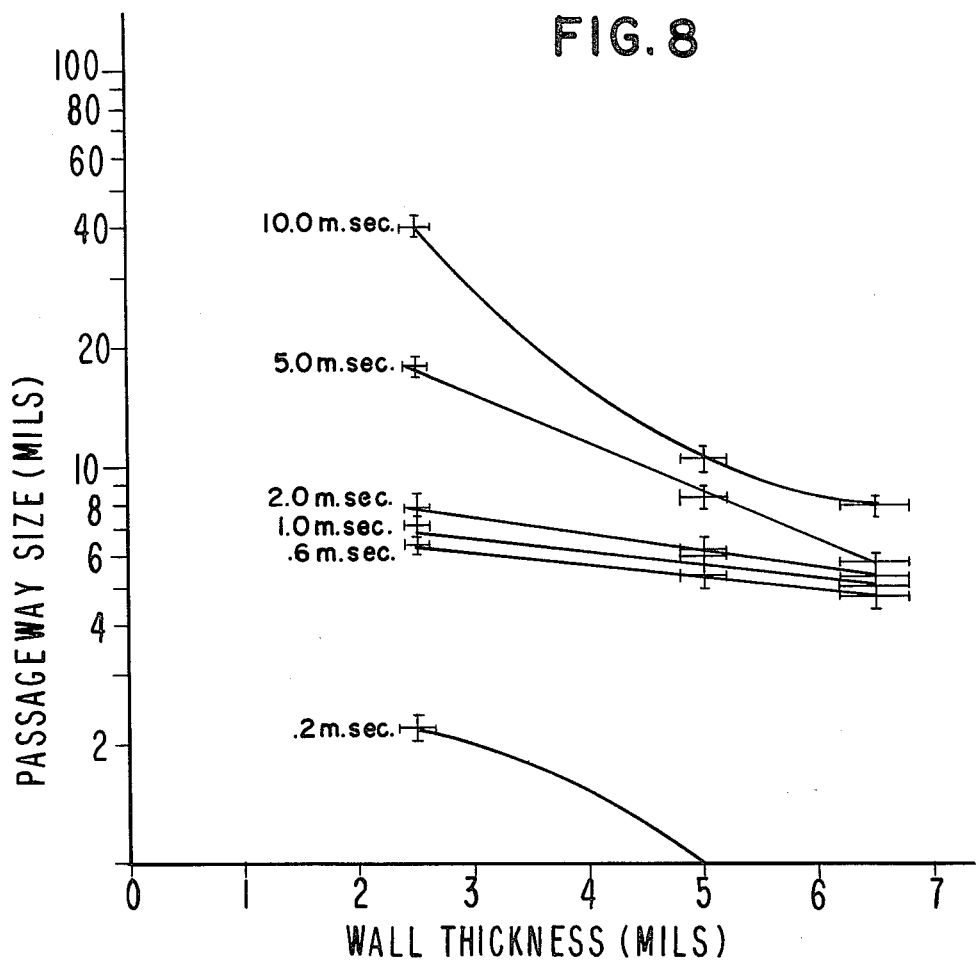

FIG. 8 shows graphically passageway size as a function of wall thickness at various firing durations. The plots of FIG. 8 were developed with the $CO_2$ laser described above set at 50 watts power. The LFD was LFD*. Passageways were formed in cellulose acetate walls 65, 130 and 165 microns thick at the indicated firing durations and were measured with an optical comparator.

Figure 9:
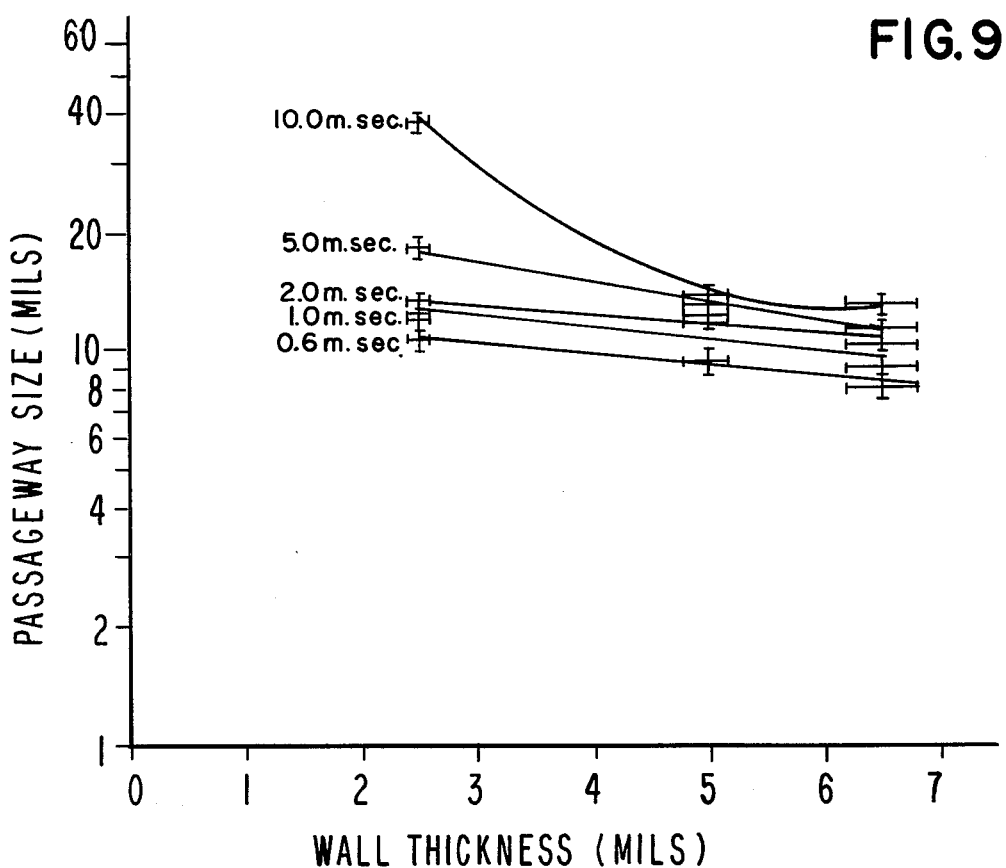
Figure 10:
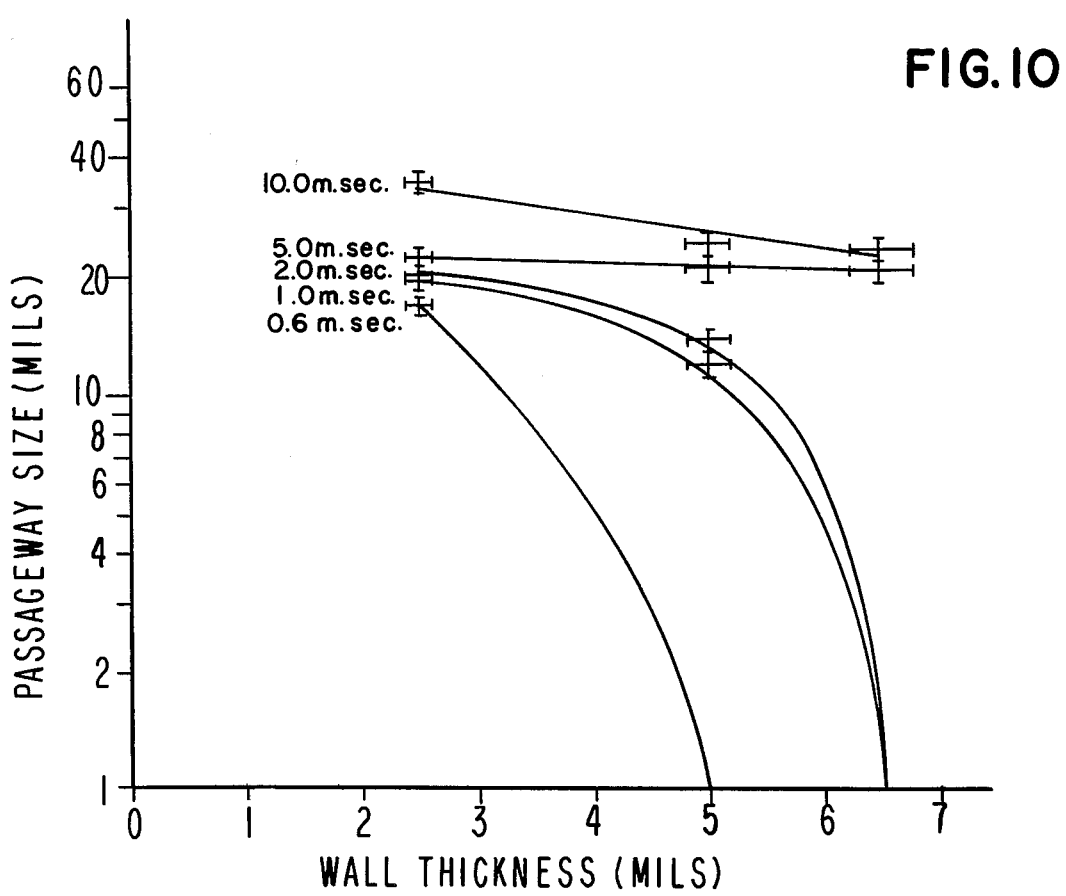

The graphs of FIGS. 9 and 10 were made in the same manner LFD vernier readings of 0.15 and 0.20, respectively (see FIG. 7) were used.

The graphs of FIGS. 7-10 illustrate the relationship between the above mentioned process variables except laser power. Passageway size will increase with increasing laser power, all other variables being held constant.

Modifications of the above described process which are obvious to those of skill in the mechanical, laser and/or pill handling arts are intended to be within the scope of the following claims.

We claim:

1. A process for forming outlet passageways of accurate predetermined size in the walls of pills which dispense their contents by osmotically pumping said contents out said outlet passageway comprising:
   (a) moving the pills in succession along a predetermined path at a predetermined velocity;

(b) tracking the moving pills seriatim at said velocity with a laser of a wavelength which is absorbable by said walls by oscillating the optical path of the laser back and forth over a predetermined section of the pill path at said velocity;

(c) firing the laser during said tracking, (d) adjusting the laser beam dimension at said wall, the laser power and the firing duration such that the laser beam is capable of piercing the wall; and (e) forming, with the laser beam, an outlet passageway 4 to 2000 microns in diameter in the wall.

2. The process of claim 1 wherein step (e) forms an outlet passageway 75 to 350 microns in diameter in the wall.

3. The process of claim 1 wherein in step (a) said path is circular and in step (b) said predetermined section of said path is about 1° of arc in length.

4. The process of claim 1 wherein said walls are formed of cellulose acetate, and in step (d) said wavelength is adjusted to 9 to $12\mu$, the laser power is adjusted to 1 to 100 watts, and the firing duration is adjusted to 0.1 to 10 milliseconds.

5. The process of claim 1 wherein step (d) further includes adjusting the laser beam such that it is diverging at its point of contact with the wall.

* * * * *